US007976877B2

(12) United States Patent
Willför et al.

(10) Patent No.: US 7,976,877 B2
(45) Date of Patent: Jul. 12, 2011

(54) USE OF KNOTWOOD EXTRACTS

(75) Inventors: Stefan Willför, Åbo (FI); Christer Eckerman, Åbo (FI); Jarl Hemming, Åbo (FI); Bjarne Holmbom, Åbo (FI); Suvi Pietarinen, Åbo (FI); Anna Sundberg, Åbo (FI)

(73) Assignee: Oy Arbonova Ab, Abo (FI)

( * ) Notice: Subject to any disclaimer, the term of this patent is extended or adjusted under 35 U.S.C. 154(b) by 401 days.

(21) Appl. No.: 10/573,445

(22) PCT Filed: Oct. 21, 2004

(86) PCT No.: PCT/FI2004/000624
§ 371 (c)(1),
(2), (4) Date: Mar. 24, 2006

(87) PCT Pub. No.: WO2005/047423
PCT Pub. Date: May 26, 2005

(65) Prior Publication Data
US 2008/0124414 A1    May 29, 2008

(30) Foreign Application Priority Data

Nov. 12, 2003  (FI) ................................. 20031642

(51) Int. Cl.
*A61K 36/00* (2006.01)
*A61K 36/13* (2006.01)
*A61K 36/20* (2006.01)
(52) U.S. Cl. ......... 424/725; 424/771; 424/770; 424/769
(58) Field of Classification Search ................. None
See application file for complete search history.

(56) References Cited

U.S. PATENT DOCUMENTS

| 4,569,839 A * | 2/1986 | Grollier et al. ............ 424/74 |
| 4,708,820 A | 11/1987 | Namiki et al. ............ 252/398 |
| 5,665,367 A * | 9/1997 | Burger et al. ............ 424/401 |
| 5,968,517 A | 10/1999 | Duncan et al. ............ 424/195.1 |
| 2001/0016590 A1 * | 8/2001 | Ahotupa et al. ............ 514/310 |
| 2004/0267029 A1 * | 12/2004 | Parhi et al. ............ 549/323 |

FOREIGN PATENT DOCUMENTS

| CN | 1149468 A * | 5/1997 |
| EP | 1 342 743 | 9/2003 |
| JP | 64-42479 | 2/1989 |
| JP | 6-200286 | 7/1994 |
| JP | 7-97486 | 4/1995 |
| SU | 516722 A * | 8/1977 |
| WO | WO 99/62985 | 1/1999 |
| WO | WO 02/09893 | 2/2000 |
| WO | WO 00/59946 | 10/2000 |
| WO | WO 02/09893 A1 * | 2/2002 |
| WO | WO 02/098830 | 12/2002 |

OTHER PUBLICATIONS

Miller et al., Reinforcing plastics with Douglas-Fir bark fiber, Forest Products Journal, 24 (8): 18-23, 1974.*
Dellus et al, Polyphenol extractives in Douglas fir wood and heartwood color, Agronomique (1995), 69 (Polyphenols 94), 293-4.*
Claudot et al, Preparation and assay of chalcone synthase from walnut tree tissue, Phytochemistry, 31 (10): 3377-3380, 1992.*
Bowers, Juvenile hormone: identification of an active compound from Balsam fir, Science, 1966; 154: 1020-1021.*
Aoyama et al, Antifungal activity of (+)-juvabione and (+)-todomatuic acid against wood-destroying fungi, Hokkaido For. Prod. Res. Inst., Asahikawa, 071-01.*
Ingram et al, Knot, heartwooed, and sapwood extractives related to volatile organic compounds (VOCs) from drying southern pine lumber, Journal of wood chemistry and Technology, 20 (4): 415-439, 2000.*
Niemeyer et al, Antioxidant activities of lignans in the FRAP assay (ferric reducing/antioxidant power assay), Special Publication—Royal Society of Chemistry (2001), 269 (Biologically-Active Phytochemicals in Food), 394-395.*
Willför et al., "Antioxidant Activity of Knotwood Extractives and Phenolic Compounds of Selected Tree Species," 51 *J. Agricultural & Food Chemistry* 7600-06 (2003).

* cited by examiner

*Primary Examiner* — Qiuwen Mi
(74) *Attorney, Agent, or Firm* — James C. Lydon

(57) ABSTRACT

The use of i) finely divided knotwood, or ii) an extract, obtained by extracting knotwood with a polar solvent and recovering the extract, as an antioxidative agent. A fraction of the extract may also be used as an antioxidative agent.

10 Claims, No Drawings

USE OF KNOTWOOD EXTRACTS

FIELD OF THE INVENTION

This invention relates to the use of a knotwood extract or a fraction or a single component thereof as an antioxidative agent. Furthermore, the invention also concerns use of finely divided knotwood as an antioxidative agent.

BACKGROUND OF THE INVENTION

The publications and other materials used herein to illuminate the background of the invention, and in particular, cases to provide additional details respecting the practice, are incorporated by reference.

Knots, i.e., the branch stubs encased in the tree stem, of *Picea abies* and *Pinus sylvestris* contain exceptionally large amounts of bioactive phenolic compounds (1, 2). The amount of extractable phenolic compounds in *P. abies* knot heartwood, or knotwood for short, can be close to 30% (w/w) but is on average around 15% (w/w) (1). The amount of phenolic compounds in the knotwood is usually 50-100 times that in the stemwood. In *P. sylvestris* knotwood the amount of extractable phenolic compounds can be as large as 10%, which is several times more than in the stemwood (2). *Salix caprea* knotwood has also been shown to contain 2-10 times the amount of phenolic compounds found in the stemwood (3). In recent research at our laboratory we have found that knotwood of several other wood species, both softwood and hardwood species, follow the same pattern.

Tree materials such as heartwood, foliage, phloem, bark, and cork of several species have been found to be sources of natural phenolic antioxidants, also including tannins (4-8). However, the extract yield obtained from such materials is low and the extracts usually contain a large variety of different phenolic and non-phenolic compounds, both as glycosides and as free aglycones. The degree of glycosylation affects the antioxidant properties of phenolic compounds. For example, the antioxidant activity was found to be lower for quercetin and myricetin glycosides than for their corresponding aglycones (9). The hydrophilic compounds in softwood knots contain mainly free aglycones of lignans, oligolignans, stilbenes, and flavonoids (1, 2, 10). One or a few phenolic compounds dominate in the knotwood extracts of most softwood species. For example, more than half of the hydrophilic extractives of *P. abies* knotwood are lignans, the rest being mainly oligolignans, while the two isomers of hydroxymatairesinol constitute over 70% of the lignans (1, 10). Hydroxymatairesinol, extracted and purified from *P. abies* knotwood, has been found to be a very strong antioxidant in vitro (11).

It is possible to separate most of the knotwood from the over-sized chip fraction in a pulp mill (12). This could be done in order to utilize the extractives found in the knotwood and, at the same time, increase the pulp quality, since wood knots are detrimental during pulping and papermaking. The phenolic compounds could be extracted (13) and, if necessary, purified by chromatographic methods.

Certain phenolic compounds have earlier been suggested for use as antioxidative agents for use in therapy or in food additives. As example can be mentioned the lignan hydroxymatairesinol, the antioxidative use of which is disclosed in WO 00/59946. Also other lignans such as matairesinol have been suggested as antioxidants for medical or cosmetic use.

According to our knowledge, knotwood extracts or fractions thereof have not earlier been suggested as antioxidative agents. Moreover, single lignans or other phenolic compounds, or juvabiones, have not earlier been suggested for use as antioxidants for technical purposes.

SUMMARY OF THE INVENTION

According to one aspect, the present invention relates to the use of finely divided knotwood as an antioxidative agent.

According to another aspect, the present invention relates to the use of an extract, obtained by extracting knotwood with a polar solvent and recovering the extract, as an antioxidative agent.

According to a third aspect, the inventions concerns the use of a fraction of an extract, said extract being obtained by extracting knotwood with a polar solvent and recovering the extract followed by withdrawal of at least one component, as an antioxidative agent.

According to a fourth aspect, this invention concerns the use of a single phenolic compound or juvabione, derived from an extract, obtained by extracting knotwood with a polar solvent and recovering the extract, and purifying the extract, as a technical antioxidant to prevent oxidative deterioration caused by heat, light or oxygen in elastomers, plastics, petrols, bio-oils; for stabilization of lubricants against oxidation, as antioxidant in adhesives, in food, in cosmetics, in packing, in paints and dispersions; as biocides, especially fungicides, bactericides or insecticides; as wood preservatives or in paper to prevent yellowing.

DETAILED DESCRIPTION OF THE INVENTION

The basis for this invention is an investigation where we applied three different antioxidant tests to 13 well-defined hydrophilic knotwood extracts or fractions of the same, derived from commercially important wood species. Surprisingly, when the antioxidative properties of the extracts or fractions thereof were compared to antioxidative properties of pure wood-derived phenolic compounds, it was found that the extracts as such or fractions of the same were more effective antioxidative substances than the single phenolic compounds.

A method for isolating of phenolic substances or juvabiones by extraction of knotwood is described in WO 02/098830.

The term "phenolic substances" shall be understood to cover lignans, oligolignans, flavonoids, isoflavonoids, stilbenes, tannins and phenolic acids. All these groups are mainly hydrophilic substances that can be extracted with polar, i.e. hydrophilic solvents.

The term "knotwood" shall be understood to include the "knots", i.e. the part of the branches that is embedded in the stem, and the branches extending outwards from the stem.

Important industrially applicable sources of knotwood are oversized chips or a knotwood-rich subfraction thereof. Also certain knotwood-rich residues obtained in finishing of mechanical wood products can be used. Such residues include, for example, the plywood sheet pieces which include knots and are cut out and replaced by corresponding pieces of normal plywood in the manufacturing stage before the individual plywood sheets are pasted together to form the finished product. Other examples are pieces of planks and boards rich in knots and therefore rejected for various reasons in building and construction, in furniture industry and the like. Also sawdust is an example of such residues.

The "over-sized chip fraction" means the rejected fraction obtained in the screening stage of the chips aimed for the pulping process. This over-sized chip fraction, which can constitute about 1 to 5% of the total amount of wood chipped, cannot be forwarded as such to the pulping process. Up to now, this fraction has been recirculated to the chipping stage or withdrawn to be burnt. This over-sized fraction comprises in addition to knotwood also considerable amounts of "normal wood", i.e wood usable in the pulping process. The amount of knotwood in the over-sized chip fraction depends on the wood species and wood quality used, and is estimated to about 10-30%.

Although it is possible to use the over-sized chip fraction as such for extraction of phenolic substances or juvabiones, it may be preferable to first separate the material (i.e. the over-sized chips) into a knot-rich fraction and a knot-poor fraction and to use the knot-rich fraction for extraction. The "knot-poor fraction" means the "normal wood" that can be led to the pulping process. This separation can be made directly from the over-sized chip fraction, or the material can first be refined before the screening stage. An example of a suitable method for producing a knotwood-rich subfraction of oversized chips is the sedimentation method disclosed in WO 02/09893.

Because of the high concentration of phenolic compounds or juvabiones in knotwood, particularly in the knotwood-rich subfraction of oversized chips, it is possible, according to one alternative, to use finely divided, e.g. finely ground wood material as such as an antioxidative agent.

The "polar solvent" is either a single polar agent, or a mixture of two or more polar agents, where said polar agent or agents have a dielectric constant that is greater than 3, determined at 25 Celsius degrees. As examples of polar solvents can be mentioned pure water only, and mixtures of water and acetone and water and alcohol, such as water and ethanol.

The extraction can be carried out on dried wood or on raw wood material.

Although the extraction can be physically integrated with the utilization of wood in the manufacturing of pulp or mechanical wood products, the extraction can alternatively be carried out as a separate process, because the knotwood, especially the knot-rich fraction of the over-sized chips, can easily be transported and stored for later processing.

The amount of phenolic substances or juvabiones in knotwood varies greatly and depends on the phenolic substance in question and the wood species used.

In case further purification is needed, the methods to be used depend i.a. on the substance to be isolated and the desired degree of purity. As examples of useful purification methods can be mentioned chromatography or crystallization.

As examples of important wood species to be used for isolating the knotwood extracts can be mentioned *Picea abies, Betula pendula, Pinus sylvestris, Abies sibirica, Pinus sibirica, Abies balsamea, Thuja occidentalis, Pinus cembra, Pseudotsuga menziesii, Larix decidua, Picea glauca, Picea mariana, Picea pungens, Abies pectinata, Abies lasiocarpa, Pinus banksiana, Pinus resinosa, Larix lariciana, Larix sibirica, Thuja plicata, Fagus sylvatica, Populus tremula, Populus tremulus, Tsuga heterophylla* and *Pinus contorta*. However, the suitable wood species are not restricted to the aforementioned list.

As examples of important lignans which can be found in the knotwood extracts can be mentioned hydroxymatairesinol, allohydroxymatairesinol, matairesinol, conidendrin, pinoresinol, dimethyl pinoresinol, monomethyl pinoresinol, oxomatairesinol, lariciresinol, monomethyl lariciresinol, dimethyl lariciresinol, liovil, isolariciresinol, secoisolariciresinol, picearesinol, conidendric acid, hinokiresinol and nortrachelogenin. However, the term "lignans" is not restricted to these compounds.

"Oligolignans" are compounds having 3 to 6 phenylpropane units that are beta-beta linked instead of normal lignans, which have two beta-beta linked phenylpropane units. Oligolignans constitute an important group of lignans in knotwood extracts. Examples of oligolignans are secoisolariciresinol guaiacylglycerol ether, liovil guaiacylglycerol ether, hydroxymatairesinol guaiacylglycerol ether, lariciresinol guaiacylglycerol ether, 5-5-bis-secoisolariciresinol, 5-5-bis-isolariciresinol, 5-5-bis-lariciresinol, lariciresinol coumarate, secoisolariciresinol coumarate.

As examples of flavonoids which can be isolated according to the method of this invention can be mentioned pinocembrin, dihydrokaempferol, pinobanksin, naringenin, catechin, 2,4,6-trihydroxychalcone, aromadendrin and taxifolin.

As examples of stilbenes can be mentioned pinosylvin, pinosylvin monomethyl ether, dihydropinosylvin, dihydropinosylvin monomethyl ether, methylpinosylvin, methyldihydropinosylvin and resveratrol.

As examples of juvabiones can be mentioned epijuvabione, dehydrojuvabione, dihydroepijuvabione and epijuvabione acid.

The term "antioxidative agent" shall in this text be understood to cover also agents with radical scavenging capacity.

As important applications of knotwood extracts or fractions thereof as antioxidants can be mentioned technical antioxidants to prevent oxidative deterioration caused by heat, light (visible or ultraviolet) or oxygen in elastomers, plastics, petrols, bio-oils; for stabilization of lubricants against oxidation, as antioxidant in adhesives, in food, in cosmetics, in paper and packaging especially to prevent odour, in paints and dispersions; as biocides, especially fungicides, pesticides, herbicides, bactericides or insecticides; as wood preservatives or in paper to prevent yellowing. The uses are, however, not restricted to the aforementioned list.

It is also possible to use of a fraction of the total extract obtained by extracting knotwood as an antioxidative agent.

Such a fraction means, according to one embodiment, the total knotwood extract from which one or more components (i.e. phenolic substances or juvabiones) have been withdrawn, provided that the residue still comprises at least two components (i.e. two phenolic components and/or juvabiones).

According to another embodiment, the fraction means the composition comprising at least two components (phenolic compounds and/or juvabiones) having been withdrawn from the knotwood extract. An important fraction of such withdrawn compounds is, for example, oligolignans.

The fractioning of the knotwood extract can be performed according to known methods. The separation can be made, for example, by precipitation or chromatographically. Several components having similar molecule weight or similar solubility in a certain solvent can easily be withdrawn as a group.

The use of the total knotwood extract or a fraction of this extract has not previously been suggested as antioxidant. The use of such mixtures is advantageous due to the stronger effect and due to the fact that tedious purification steps are avoided. Such mixtures are particularly valuable as antioxidants in technical applications.

The use of certain lignans and flavonoids as antioxidants in medicines or in foods has been suggested. However, the single phenolic compounds or juvabiones have not previously been suggested for use as antioxidants in technical applications. One reason hereto may be the limited supply of the compounds. However, it has recently been discovered that such compounds can be isolated is considerable amounts from knotwood (WO 02/098830; WO 03/044004). Furthermore, new syntheses for production of single lignans based on the use of hydroxymatairesinol as starting material have been suggested (WO 03/057209 and WO 03/059340). Because of these new innovations, the supply of single compounds is not longer a limiting factor for their large scale use. Therefore this invention also concerns the use of a single phenolic compound or juvabione, derived from an extract, obtained by extracting knotwood with a polar solvent and recovering the extract, and purifying the extract, as a technical antioxidant to prevent oxidative deterioration caused by heat, light (visible or ultraviolet) or oxygen in elastomers, plastics, petrols, bio-oils; for stabilization of lubricants against oxidation, as antioxidant in adhesives, in packing, in paints and dispersions; as biocides, especially fungicides, bactericides or insecticides; as wood preservatives or in paper to prevent yellowing.

The invention will be illuminated by the following non-restrictive Experimental Section.

EXPERIMENTAL SECTION

Materials and Methods

Chemicals. Taxifolin ((±)-3,3',4',5,5-pentahydroxyflavanone) was obtained from Sigma-Aldrich Chemie Gmbh. (Steinhem, Germany); Trolox (6-hydroxy-2,5,7,8-tetramethylchroman-2-carboxylic acid) and butylated hydroxyanisole (BHA) from Aldrich Chemical Co. (Milwaukee, Wis., USA). All other chemicals used were of the highest quality available.

Wood material. Knotwood was sampled from full-grown trees of eleven wood species: *Picea abies* (Norway spruce, 71 growth rings at 1.5 m, several knots sampled at 14.5 m height), *Betula pendula* (silver birch, 28 growth rings, one knot at 4.2 m), and *Pinus sylvestris* (Scots pine, several knots) grown in Ekenäs, Finland; *Abies sibirica* (Siberian fir, 30 growth rings, one knot at 2.5 m) and *Pinus sibirica* (Siberian stone, 20 growth rings, four knots at 1.1 m) grown in the St. Petersburg region, Russia; *Abies balsamea* (balsam fir, 41 growth rings, one knot at 1.4 m) and *Thuja occidentalis* (northern white-cedar, 144 growth rings, two knots at 1.7 m) grown in Itasca County, Blandin Land, USA; *Pinus cembra* (Siberian stone, several knots), *Pseudotsuga menziesii* (Douglas fir, 55 growth rings, 6 knots at 16 m (tree 1); 54 growth rings, 6 knots at 20 m (tree 2)), and *Larix decidua* (European larch, 62 growth rings, two knots at 15 m) grown in Solböle, Bromarf, Finland; *Pinus contorta* (lodgepole pine, 22 growth rings, two knots at 1.9 m) grown in Sävar, Sweden. *P. sibirica* and *P. cembra* are essentially the same species. One to six knots from one tree, taken at the same height, were sampled and pooled for each species, except for *P. menziesii*, where two different trees were chosen. All knots were normal and healthy, except the knots of *B. pendula*, which contained a black inner part that was sampled. The heartwood of the knots was splintered, freeze-dried, and ground.

Preparation of knotwood extracts. Sequential extraction was carried out in an Accelerated Solvent Extractor apparatus (Dionex Corp., Sunnyvale, Calif., USA) according to Willför et al. (1). The lipophilic extractives were first extracted with hexane, and thereafter the hydrophilic extractives with an acetone:water (95:5 v/v) mixture. The extracts were stored at −18° C. The gravimetrically determined total amount of hydrophilic extractives, expressed as % of dry wood, was 20% for *Abies balsamea*, 18% for *A. sibirica*, 17% for *Picea abies*, 10% (tree 1) and 15% (tree 2) for *Pseudotsuga menziesii*, 11% for *Thuja occidentalis*, 3% for *Pinus contorta*, 16% for *P. sibirica*, and 20% for *Larix decidua*.

Preparation of *Picea abies* oligolignans. A *P. abies* knotwood extract was fractionated according to Willför et al. (10) on normal-phase silica gel columns using flash chromatography and medium-performance liquid chromatography, giving an extract containing mostly oligolignans with some lignans as the main impurity. The oligolignans consisted mainly of sesquilignans and dilignans. The oligolignans were dried and stored cold.

Preparation of *Araucaria* extract fraction. The *Araucaria* extract fraction was the residue after the isolation of secoisolariciresinol from *A. angustifolia* knotwood. The extract fraction was dried and stored cold.

Preparation of *Pinus cembra* stilbenes. The *P. cembra* stilbenes were prepared from *P. cembra* knotwood by extraction with acetone in a large Soxhlet apparatus. The lipophilic extractives were then removed by refluxing the dry acetone extract with hexane. The residue containing mainly stilbenes was dried and stored cold.

Preparation of *Betula pendula* extract fraction. The *B. pendula* extract fraction was prepared from a hydrophilic extract of the black inner part of knotwood by flash chromatography on normal-phase silica gel columns (15 cm×40 mm i.d.) using dichloromethane:ethanol as eluent. The extract fraction was dried and stored cold.

Preparation of hydroxymatairesinol. Hydroxymatairesinol was prepared from *P. abies* knotwood by extraction with acetone in a large Soxhlet apparatus. Hydroxymatairesinol was fractionated from the hydrophilic extract by flash chromatography on normal-phase silica gel columns using dichloromethane:ethanol as eluent.

Preparation of secoisolariciresinol. Secoisolariciresinol was prepared from *A. angustifolia* knotwood by extraction with acetone in a large Soxhlet apparatus. Secoisolariciresinol was fractionated from the hydrophilic extract by flash chromatography on normal-phase silica gel columns using dichloromethane:ethanol as eluent. The purified secoisolariciresinol was further recrystallized from dilute 2-propanol.

Preparation of nortrachelogenin. Nortrachelogenin was prepared from *P. sylvestris* knotwood by extraction first with hexane and then with acetone in a large Soxhlet apparatus. Nortrachelogenin was fractionated from the hydrophilic extract by flash chromatography on normal-phase silica gel columns using dichloromethane:ethanol as eluent.

Preparation of lariciresinol. Lariciresinol was prepared from *A. balsamea* knotwood by extraction with acetone in a large Soxhlet apparatus. Lariciresinol was fractionated from the hydrophilic extract by flash chromatography on normal-phase silica gel columns using dichloromethane:ethanol as eluent. The purified lariciresinol was recrystallized from cyclohexane/ethanol.

Preparation of matairesinol. Matairesinol was prepared from isolated hydroxymatairesinol according to Eklund et al. (14).

Preparation of extracts and compounds for antioxidant tests and analysis. The extracts and pure compounds were dissolved in 5-12 mL of ethanol, giving a concentration of 3-26 mg dry extract/mL and then filtered using 0.2-μm syringe filters. 300-μL aliquots were taken for chemical characterization.

Analysis by gas chromatography (GC) and GC-mass spectrometry (MS). Lignans, stilbenes, flavonoids, and juvabiones were analyzed on a 25 m×0.20 mm i.d., 0.11 μm HP-1 capillary column coated with crosslinked methyl polysiloxane (Agilent Technologies, Palo Alto, Calif., USA). The gas chromatograph was a Perkin Elmer AutoSystem XL instrument (Perkin Elmer, Boston, Mass., USA). Column oven: 120° C.-6° C./min-300° C. (10 min); carrier gas $H_2$ (20 mL/min); split injector (1:20) 260° C.; FID detector 300° C.; injection volume 1 μL. The ethanol was evaporated and the extractives were silylated by addition of 80 μL bis-(trimethylsilyl)-trifluoroacetamide, 20 µL trimethylchlorosilane, and 20 µL pyridine. The reaction was completed by keeping the test tubes in an oven at 70° C. for 1 h. Heneicosanoic acid and betulinol were used as internal standards. The method used was according to Ekman and Holmbom (15). A correction factor of 1.2 was used for the lignans that were calculated against betulinol (1). Oligolignans were quantified on a short 6 m×0.53 mm i.d., 0.15 µm HP-1 column using cholesteryl heptadecanoate and 1,3-dipalmitoyl-2-oleyl glycerol as internal standards (16). The gas chromatograph was a Varian 3400 instrument (Varian Inc., Palo Alto, Calif., USA). Column oven: 100° C. (1.5 min), 12° C./min-340° C. (5 min); carrier gas $H_2$ (20 mL/min); SPI (Septum equipped Programmable Injector) 80° C. (0.5 min)-200° C./min-340° C. (18 min); FID detector 340° C.; injection volume 0.4 µL. Identification of individual components was performed by GC-MS analysis of the silylated components with an HP 6890-5973 GC-quadruple-MSD instrument. Both a similar 25 m HP-1 GC column as above and a 15 m×0.25 mm i.d., 0.1 µm MXT-65TG column (Restek Corp., USA), which allowed elution of the silylated oligolignans (10), were used.

Antioxidative Potency

Estimation of inhibition of lipid peroxidation. The antioxidant properties of the extracts, fractions thereof and the pure compounds were estimated by their potency to inhibit t-butylhydroperoxide (t-BuOOH) induced lipid peroxidation in rat liver microsomes in vitro (17) and by their capacity to trap superoxide (oxygen radical) and peroxyl radicals, estimated by chemiluminescence-based methodology (17). The lipid peroxidation was detected by luminol-enhanced chemiluminescence. Test compounds or extracts were added to incubation mixtures in a small volume (2% of incubation volume), and the lipid peroxidation potency was compared to that of the vehicle (ethanol). Assays for the t-BuOOH-initiated lipid peroxidation was performed as follows. The buffer (50 mM sodium carbonate, pH 10.2, with 0.1 mM EDTA) was pipetted in a volume of 0.8 mL in the luminometer cuvette. 20 µL of diluted rat liver microsomes (final concentration 1.5 µg protein/mL) was added, followed by 6 µL of luminol (0.5 mg/mL) and test chemicals. The reaction was initiated by 0.05 mL of 0.9 mM t-BuOOH at 33° C. The chemiluminescence was measured for 45 min at 1 min cycles. The tests were repeated two to four times on separate days. Variation between assays were <10%.

Estimation of free radical trapping capacity. The capacity of the extracts, fractions thereof and the pure compounds to trap superoxide (oxygen radical) and peroxyl radicals was estimated by chemiluminescence-based methodology (17). Superoxide anions were produced by xanthine-xanthine oxidase system as follows. 20 µL of xanthine oxidase (420 mU/mL), 0.02 mL of 5 mM lucigenin, 0.02 mL of 200 mM linoleic acid dissolved in 50 mM KOH, 0.78 mL of 50 mM potassium phosphate buffer, pH 10.0, and test samples were pipetted in cuvettes. The reaction was initiated by the automated dispensing of 0.11 mL of 1.45 mM xanthine (final volume 1.0 mL). Chemiluminescence in duplicate samples at 35° C. was measured for 6 min in 1-min cycles. Peroxyl radicals were generated by thermal decomposition of 2,2'-azobis(2-amidinopropane)-hydrochloride as follows. 0.45 mL of 0.1 M sodium phosphate buffer, pH 7.4, containing 0.9% NaCl, 0.02 mL of 120 mM linoleic acid, 0.05 mL of luminol (0.5 mg/mL) and test compounds were mixed in the cuvette. The assay was initiated by 0.05 mL of ABAP (83 mg/mL). Chemiluminescence in triplicate cuvettes at 37° C. was measured until a peak value for each sample was detected. The half-peak time point defined the peroxyl radical trapping capacity.

Results

Total amount of hydrophilic extractives. The total amount of hydrophilic knotwood extractives was considerable, being 10-20% of the dry wood, from most of the investigated wood species. The amount was smaller from the Pinus contorta knotwood, being only 3%. It should be kept in mind that these numbers represent only a few knots in a tree. However, it has been found that knotwood in general contains exceptionally large amounts of hydrophilic extractives, even though the natural variation between different knots and trees can be large (1-3).

Chemical composition of the hydrophilic extracts and fractions. Lignans and oligolignans (mainly sesquilignans and dilignans) were the main compounds in the Abies, Picea, and Larix extracts and in the Araucaria extract fraction, constituting at least half of the extracts (Table 1). The lignans also dominated in one of the two Pseudotsuga extracts and the Thuja extract, while flavonoids or stilbenes dominated in the other extracts. Only the Pinus extracts contained stilbenes.

A few lignans dominated in all extracts (Table 1; Scheme 1). The Picea abies knotwood contained mainly hydroxymatairesinol, about 7% (w/w), while the Abies and Larix knotwood contained much secoisolariciresinol. The main lignans in Thuja occidentalis knotwood were slightly different since they have additional methoxyl and hydroxyl groups in their structure (18), compared to the lignans in the other extracts. The oligolignans were a group of compounds consisting mainly of guaiacylglycerol ethers of the main lignans in the Abies, Picea, Larix, and Pinus sibirica extracts. An example of an oligolignan is shown in Scheme 2. Such compounds have recently been characterized in Picea abies and Pinus sylvestris knotwood extracts (1, 2, 10). However, no such compounds were detected in the Pseudotsuga or Pinus contorta extracts, even though the GC elution time suggested the presence of oligomeric substances in the extracts. The Thuja oligomers were not identified either, but these were probably oligolignans derived from the thujalignans. The oligomeric substances should be further characterized in these extracts.

A few pinosylvins dominated among the stilbenes in the Pinus extracts and in the P. cembra fraction (Table 1; Scheme 3). Pinosylvin monomethyl ether and dihydropinosylvin monomethyl ether were the most abundant stilbenes. Taxifolin and pinocembrin, both representing the flavanone type of compounds, were the main flavonoids (Table 1; Scheme 4). Some juvabiones were present in the Abies extracts and in one of the Pseudotsuga extracts (Table 1; Scheme 2). The Araucaria extract fraction also contained a norlignan, hinokiresinol, which was not found in any other extract. The Betula pendula extract fraction contained stilbene-derived compounds. However, the exact structure of this compound group is still to be determined. No substantial amounts of polymeric compounds were present in the extracts.

Composition of the isolated and synthesized phenolic compounds. Two batches of the lignans hydroxymatairesinol, lariciresinol, secoisolariciresinol, and nortrachelogenin were isolated, while one batch of matairesinol was synthesized. The chemical composition of the isolated or synthesized lignans, as well as of the purchased taxifolin, was determined by GC analysis. The GC-purity of the compounds was over 95%, except for the second batch of secoisolariciresinol, which had a GC-purity of about 92%. The main impurity, constituting about 4% of the extract, was monomethyl secoisolariciresinol. The isolated hydroxymatairesinol consisted of two epimers, 7S,8R,8'R-hydroxymatairesinol (92%) and 7R,8R,8'R-allo-hydroxymatairesinol (8%). The structure of these epimers was recently unambiguously proven (19).

Inhibition of lipid peroxidation in vitro. The antioxidative potency of the extracts was, according to one alternative, estimated on the basis of their potency to inhibit t-BuOOH induced lipid peroxidation in rat liver microsomes in vitro. Eleven of the 13 tested knotwood extracts had a higher antioxidative potency than the synthetic antioxidant BHA ($IC_{50}$ 198 µg/L), while only the *Thuja* and one of the *Pseudotsuga* extracts had a lower antioxidative potency (Table 2). The *Pinus contorta* knotwood extract especially, but also the two *Abies* and one of the *Pseudotsuga* extracts, had an antioxidative potency almost similar to that of Trolox ($IC_{50}$ 5.0 µg/L). The isolated lignans and taxifolin all had a high antioxidative potency close to that of Trolox and higher than that of BHA. The antioxidant potency of hydroxymatairesinol was well in range with the earlier work of Saarinen et al. (11). The differences in the obtained antioxidative potency between the lignans in series 1 and 2 are probably due to the facts that the assays were done on two different batches of rat liver microsomes, and the time between the assays was about 6 months.

The high antioxidant potency of some of the knotwood extracts indicates synergistic effects between the different phenolic compounds present, since the antioxidant potency of several of the knotwood extracts was higher than that of the predominant pure compounds (Table 2). However, it is possible that small amounts of non-analyzed and non-identified compounds contributed much to the antioxidant potency. The *Pinus contorta* knotwood extract contained the flavanone type compounds pinocembrin and pinobanksin, as well as pinosylvin monomethyl ether and pinosylvin, as the main compounds (Table 1). Flavanone type compounds, such as taxifolin, and pinosylvin and related compounds have been shown to be good inhibitors of lipid peroxidation in vitro (20-22). The main compound in the *Pseudotsuga menziesii* 1 extract was taxifolin, while the *Abies* extracts contained the lignans secoisolariciresinol and lariciresinol and some oligolignans. These three extracts were also the only ones that contained juvabiones. Even though the amounts of juvabiones were small, it cannot be ruled out that these compounds contributed much to the antioxidant potency. It is interesting to note the relatively low antioxidant potency of the *Pinus* cembra stilbenes and the *P. sibirica* extract (Table 2). This indicates that the pinosylvin type compounds were not effective inhibitors of lipid peroxidation in this specific test, even though this type of compounds have been shown earlier to be good inhibitors of lipid peroxidation in vitro (23). Neither the thujalignan type compounds nor the lignan isolariciresinol, dominating the *Thuja occidentalis* and *Pseudotsuga menziesii* 2 extracts, respectively, were good inhibitors of lipid peroxidation in this test.

Scavenging of superoxide radicals in vitro. The capacity of the extracts and the pure compounds to scavenge superoxide radicals was estimated by chemiluminescence-based methodology. All extracts, except that of *Pinus sibirica* and the *Araucaria* extract fraction, were at least fairly good scavengers of superoxide radicals in this test (Table 3). The *Pinus cembra* stilbenes ($IC_{50}$ 0.84 µg/L) and the *Picea abies* oligolignans ($IC_{50}$ 0.93 µg/L) were even more effective scavengers of superoxide radicals than both BHA ($IC_{50}$ 2.7 µg/L) and Trolox ($IC_{50}$ 6.3 µg/L). Of the pure compounds, taxifolin, nortrachelogenin, and secoisolariciresinol were more effective scavengers than both BHA and Trolox. Only hydroxymatairesinol ($IC_{50}$ 81 µg/L) showed a very ineffective scavenging of the superoxide radicals.

The synergistic effect that was suggested for the inhibition of the lipid peroxidation was not observed for the scavenging of superoxide radicals. On the contrary, pure compounds and fractions containing mainly stilbene and oligolignan type compounds were the most effective scavengers (Table 3). However, the scavenging capacity of the *Pinus sibirica* extract was lower than expected ($IC_{50}$ 171 µg/L), considering that the main compounds in the extract were stilbenes similar to the *Pinus cembra* stilbenes. The large difference in the superoxide radical scavenging capacity of the lignans hydroxymatairesinol and nortrachelogenin and matairesinol is also surprising, since the structures of these compounds are quite similar (Scheme 1).

Scavenging of peroxyl radicals in vitro. The capacity of the extracts and the pure compounds to scavenge peroxyl radicals was estimated by chemiluminescence-based methodology. The *Pinus contorta* knotwood extract was an effective scavenger of peroxyl radicals (trapping capacity 47 mmole/g) compared to Trolox (trapping capacity 8.0 mmole/g), while the capacity of most of the other extracts was similar to that of Trolox (Table 4). Only the *Thuja occidentalis* and the *Pseudotsuga menziesii* 2 extracts had a low peroxyl scavenging capacity (trapping capacity 2.4 mmole/g and 1.1 mmole/g, respectively). Of the pure compounds, taxifolin was the most effective scavenger of peroxyl radicals (stoichiometric factor 4.7 mole/mole), while also secoisolariciresinol was an effective scavenger (stoichiometric factor 3.1-4.0 mole/mole). The effect of the other lignans was similar to that of Trolox (stoichiometric factor 1.7-2.0 mole/mole).

The relative effect of the different extracts in the peroxyl radical scavenging test was similar to the relative potency to inhibit t-BuOOH induced lipid peroxidation, with the *Pinus contorta* extract as the most effective one in both tests (Tables 2 and 4). The *Pinus cembra* stilbenes and the stilbene-rich *Pinus sibirica* extract had a slightly lower scavenging capacity compared to Trolox (Table 4). The pinosylvin-related stilbenes resveratrol and pterostilbene have been reported to be more effective peroxyl radical scavengers than Trolox (23).

The above study showed that the hydrophilic extracts of knotwood of selected industrially important softwood and hardwood species, or fractions of the same, have a high antioxidative potency compared to the well-known antioxidant Trolox and to the synthetic antioxidant BHA. It was also shown that pure wood-derived lignans and the flavonoid taxifolin had a high antioxidative potency. The hydrophilic knotwood extracts were also quite pure in the sense that only a few compounds, belonging to the groups of lignans, oligolignans, pinosylvins, or flavonoids, strongly dominated in each extract. The extracts, or fractions thereof seem to have synergistic effects since the antioxidant potency of several of the knotwood extracts or extract fractions were higher than that of the predominant compounds in these extracts or fractions.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

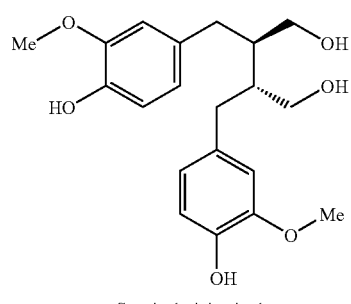

Scheme 1

Secoisolariciresinol

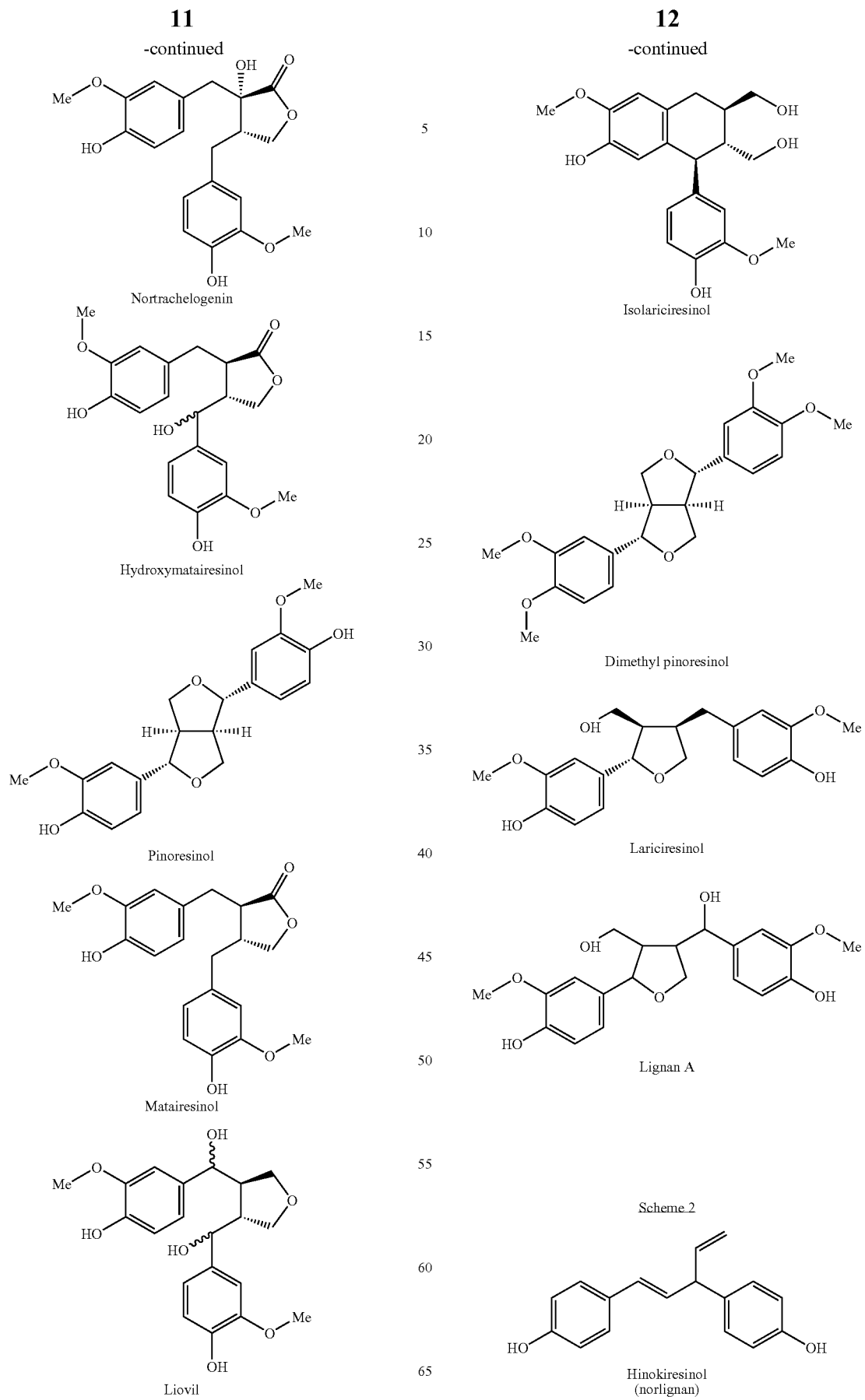

-continued
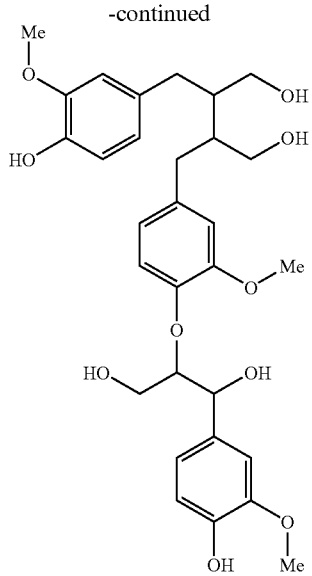
Secoisolariciresinol
guaiacylglycerol ether
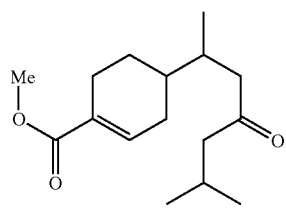
Juvabione
(Basic structure)
Scheme 3
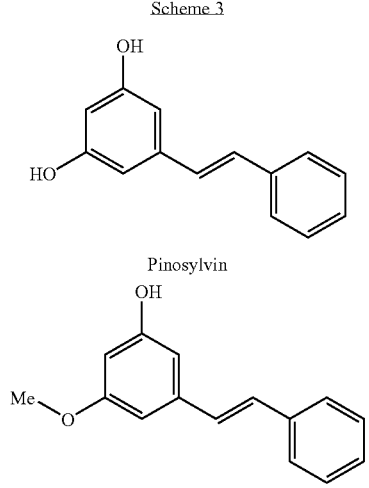
Pinosylvin
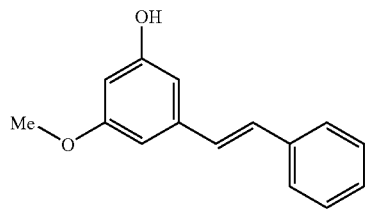
Pinosylvin monomethyl ether
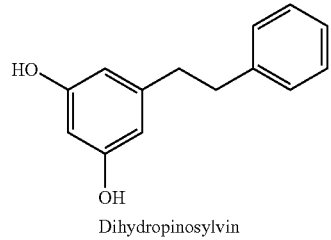
Dihydropinosylvin
-continued
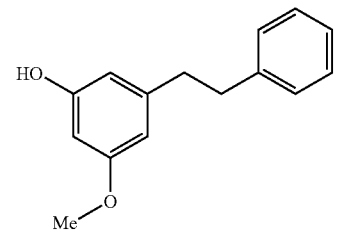
Dihydropinosylvin
monomethyl ether
Scheme 4
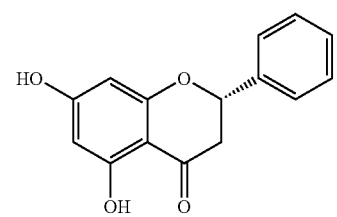
Pinocembrin
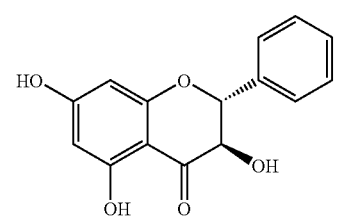
Pinobanksin
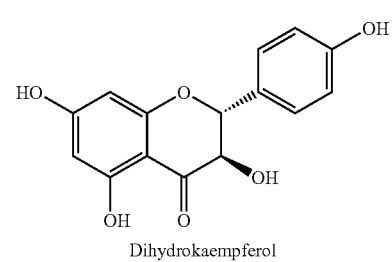
Dihydrokaempferol
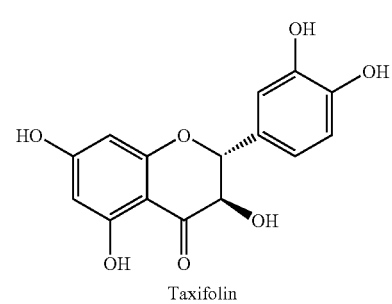
Taxifolin

TABLE 1

Main component groups and compounds in the hydrophilic knotwood extracts and fractions of extracts

| Wood species | Composition[a] | (% of gravimetric extract) | Wood species | Composition[a] | (% of gravimetric extract) |
|---|---|---|---|---|---|
| *Abies balsamea* | Lignans | 33 | *Pinus contorta* | Lignans | 10 |
|  | Secoisolariciresinol | 18 |  | Nortrachelogenin | 5 |
|  | Lariciresinol | 9 |  | Liovil | 3 |
|  | Oligolignans | 19 |  | Oligomers | 3 |
|  | Juvabiones | 2 |  | Flavonoids | 20 |
| *Abies sibirica* | Lignans | 33 |  | Pinocembrin | 15 |
|  | Secoisolariciresinol | 21 |  | Pinobanksin | 7 |
|  | Lariciresinol | 7 |  | Stilbenes | 15 |
|  | Oligolignans | 31 |  | Pinosylvin monomethylether | 9 |
|  | Juvabiones | 3 |  | Pinosylvin | 6 |
| *Picea abies* | Lignans | 53 | *Pinus sibirica* | Lignans | 26 |
|  | Hydroxymatairesinol | 41 |  | Lariciresinol | 19 |
|  | Secoisolariciresinol | 3 |  | Isolariciresinol | 3 |
|  | α-conidendrin | 3 |  | Secoisolariciresinol | 2 |
|  | Oligolignans | 12 |  | Oligolignans | 6 |
| *Pseudotsuga menziesii* 1[b] | Lignans | 9 |  | Flavonoids | 7 |
|  | Nortrachelogenin | 4 |  | Pinocembrin | 6 |
|  | Lariciresinol | 2 |  | Stilbenes | 46 |
|  | Oligomers | 6 |  | Pinosylvin monomethylether | 25 |
|  | Flavonoids | 42 |  | Dihydropinosylvin monomethylether | 15 |
|  | Taxifolin | 41 |  | Pinosylvin | 3 |
|  | Juvabiones | 3 |  | Dihydropinosylvin | 2 |
| *Pseudotsuga menziesii* 2[b] | Lignans | 45 | *Larix decidua* | Lignans | 40 |
|  | Isolariciresinol | 31 |  | Secoisolariciresinol | 24 |
|  | Secoisolariciresinol | 9 |  | Lariciresinol | 7 |
|  | Oligomers | 7 |  | Isolariciresinol | 6 |
|  | Flavonoids | 1 |  | Oligolignans | 18 |
|  | Taxifolin | 1 |  | Flavonoids | 17 |
| *Thuja occidentalis* | Thujalignans[c] | 25 |  | Taxifolin | 14 |
|  | Oligomers | 2 |  | Dihydrokaempferol | 3 |
| *Araucaria* extract fraction | Lignans | 48 | *Pinus cembra* stilbenes | Pinosylvins | 68 |
|  | Dimethyl pinoresinol | 15 |  | Pinosylvin monomethyl ether | 43 |
|  | Lariciresinol | 15 |  | Dihydropinosylvin monomethyl ether | 24 |
|  | Pinoresinol | 9 | *Picea abies* oligolignans | Oligolignans | 70 |
|  | Monomethyl pinoresinol | 3 |  | Lignans | 16 |
|  | Hinokiresinol (norlignan) | 3 |  | Liovil + lignan A | 15 |
|  | Monomethyl lariciresinol | 2 |  |  |  |
|  | Dimethyl lariciresinol | 1 |  |  |  |

[a]Compound groups and major compounds present in 1% or more.
[b]Two different trees
[c]Several unidentified lignans, probably related to thujaplicatin and 4-O-demethylyatein + small amounts of matairesinol and lignan A.

TABLE 2

Inhibition of lipid peroxidation in vitro, expressed as $IC_{50}$ values (i.e. concentration of extract that inhibits lipid peroxidation by 50%), by the knotwood extracts, fractions, two different series of lignans, taxifolin, and reference compounds

| Sample | $IC_{50}$ (μg/L) | $IC_{50}$ (μM) |
|---|---|---|
| Trolox (reference) | 5.0 |  |
| *Pinus contorta* | 8.1 |  |
| *Abies sibirica* | 16 |  |
| *Abies balsamea* | 18 |  |
| *Pseudotsuga menziesii* 1 | 18 |  |
| *Betula pendula* extract fraction | 32 |  |
| *Picea abies* | 45 |  |
| *Picea abies* oligolignans | 52 |  |
| *Larix decidua* | 57 |  |
| *Araucaria* extract fraction | 97 |  |
| *Pinus cembra* stilbenes | 132 |  |
| *Pinus sibirica* | 132 |  |
| BHA (reference) | 198 |  |
| *Pseudotsuga menziesii* 2 | 219 |  |
| *Thuja occidentalis* | 447 |  |
| Series 1[a] |  |  |
| Trolox (reference) | 5.0 | 0.02 |
| Secoisolariciresinol | 37 | 0.10 |
| Taxifolin | 46 | 0.15 |
| Nortrachelogenin | 53 | 0.14 |
| Hydroxymatairesinol | 58 | 0.15 |
| Matairesinol | 99 | 0.28 |
| Lariciresinol | 126 | 0.35 |
| BHA (reference) | 198 | 1.1 |
| Series 2[a] |  |  |
| Trolox (reference) | 46 | 0.18 |
| Secoisolariciresinol | 54 | 0.15 |
| Lariciresinol | 63 | 0.17 |
| Hydroxymatairesinol | 67 | 0.18 |
| Nortrachelogenin | 70 | 0.19 |

[a]Different test series

TABLE 3

Scavenging of superoxide radicals in vitro, expressed as IC$_{50}$ values (i.e. concentration of extract required for scavenging of 50% of the radicals), by the knotwood extracts, fractions, lignans, taxifolin, and reference compounds

| Sample | IC$_{50}$ (µg/L) | IC$_{50}$ (nM) |
|---|---|---|
| *Pinus cembra* stilbenes | 0.84 | |
| *Picea abies* oligolignans | 0.93 | |
| BHA (reference) | 2.7 | |
| Trolox (reference) | 6.3 | |
| *Abies sibirica* | 15 | |
| *Pseudotsuga menziesii* 2 | 22 | |
| *Picea abies* | 23 | |
| *Pseudotsuga menziesii* 1 | 31 | |
| *Thuja occidentalis* | 33 | |
| *Betula pendula* extract fraction | 34 | |
| *Larix decidua* | 35 | |
| *Pinus contorta* | 51 | |
| *Abies balsamea* | 57 | |
| *Araucaria* extract fraction | 74 | |
| *Pinus sibirica* | 171 | |
| Series 1 | | |
| Taxifolin | 0.16 | 0.51 |
| Nortrachelogenin | 0.53 | 1.4 |
| Secoisolariciresinol | 1.8 | 4.8 |
| BHA (reference) | 2.7 | 15 |
| Trolox (reference) | 6.3 | 25 |
| Lariciresinol | 13 | 35 |
| Matairesinol | 14 | 40 |
| Hydroxymatairesinol | 81 | 217 |

TABLE 4

Scavenging of peroxyl radicals in vitro, expressed as the trapping capacity (i.e. mmoles of peroxyl radicals scavenged per gram of extract) and as the stoichiometric factor (i.e. mmoles of peroxyl radicals scavenged per mole of compound), by the knotwood extracts, fractions, two different series of lignans, taxifolin, and reference compounds

| Sample | Trapping capacity (mmole/g) | Stoichiometric factor (mole/mole) |
|---|---|---|
| *Pinus contorta* | 47 | |
| *Abies sibirica* | 15 | |
| *Pseudotsuga menziesii* 1 | 12 | |
| *Abies balsamea* | 9.6 | |
| *Betula pendula* extract fraction | 8.2 | |
| Trolox (reference) | 8.0 | |
| *Larix decidua* | 6.4 | |
| *Araucaria* extract fraction | 5.9 | |
| *Picea abies* | 4.8 | |
| *Pinus cembra* stilbenes | 4.2 | |
| *Picea abies* oligolignans | 4.2 | |
| *Pinus sibirica* | 3.2 | |
| *Thuja occidentalis* | 2.4 | |
| *Pseudotsuga menziesii* 2 | 1.1 | |
| Series 1[a] | | |
| Taxifolin | 16 | 4.7 |
| Secoisolariciresinol | 8.5 | 3.1 |
| Trolox (reference) | 8.0 | 2.0 |
| Nortrachelogenin | 5.9 | 2.2 |
| Hydroxymatairesinol | 5.6 | 2.1 |
| Matairesinol | 2.9 | 1.0 |
| Lanciresinol | 2.7 | 1.0 |
| Series 2[a] | | |
| Secoisolariciresinol | 11 | 4.0 |
| Hydroxymatairesinol | 7.3 | 2.7 |
| Lariciresinol | 7.3 | 2.6 |
| Trolox (reference) | 6.8 | 1.7 |
| Nortrachelogenin | 5.3 | 2.0 |

[a]Different test series

REFERENCES (1) Willför, S.; Hemming, J.; Reunanen, M.; Eckerman, C.; Holmbom, B. Lignans and lipophilic extractives in Norway spruce knots and stemwood. *Holzforschung* 2003, 57, 27-36.

(2) Willför, S.; Hemming, J.; Reunanen, M.; Holmbom, B. Phenolic and lipophilic extractives in Scots pine knots and stemwood. *Holzforschung* 2003, 57, 359-372.

(3) Pohjamo, S. P.; Hemming, J. E., Willför, S. M.; Reunanen, M. H. T.; Holmbom, B. R. Phenolic extractives in *Salix caprea* wood and knots. *Phytochemistry* 2003, 63, 165-169.

(4) Kähkönen, M. P.; Hopia, A. I.; Vuorela, H. J.; Rauha, J.-P.; Pihlaja, K.; Kujala, T. S.; Heinonen, M. Antioxidant activity of plant extracts containing phenolic compounds. *J. Agric. Food Chem.* 1999, 47, 3954-3962.

(5) Chang, S.-T.; Wu, J.-H.; Wang, S.-Y.; Kang, P.-L.; Yang, N.-S.; Shyur, L.-F. Antioxidant activity of extracts from *Acacia confusa* bark and heartwood. *J. Agric. Food Chem.* 2001, 49, 3420-3424.

(6) Shimizu, K.; Kondo, R.; Sakai, K. Antioxidant activity of heartwood extracts of Papua New Guinea woods. *J. Wood Sci.* 2002, 48, 446-450.

(7) Arima, Y.; Hatanaka, A.; Fujimoto, K.; Fukuda, K.; Sakurai, H. Scavenging activity of α-, β- and γ-thuijaplicin against active oxygen species. *Chem. Pharm. Bull.* 1997, 45, 1881-1886.

(8) Kai, Y. Chemistry of extractives. In *Wood and Cellulosic Chemistry*, First edition; Hon, D. N.-S., Shiraishi, N, Eds.; Marcel Dekker: New York, N.Y., 1990; pp. 215-255.

(9) Hopia, A. I.; Heinonen, M. Antioxidant activity of flavonol aglycones and their glycosides in methyl linoleate. *J. Am. Oil Chem. Soc.* 1999, 76, 139-144.

(10) Willför, S.; Reunanen, M.; Eklund, P.; Sjöholm, R.; Kronberg, L.; Fardim, P.; Pohjamo, S.; Holmbom, B. Oligolignans in Norway spruce and Scots pine knots and Norway spruce stemwood. Submitted to *Holzforschung*.

(11) Saarinen, N. M.; Wärri, A.; Mäkelä, S. I.; Eckerman, C.; Reunanen, M.; Ahotupa, M.; Salmi, S. M.; Franke, A. A.; Kangas, L.; Santti, R. Hydroxymatairesinol, a novel enterolactone precursor with antitumor properties from coniferous tree (*Picea abies*). *Nutr. Cancer* 2000, 36, 207-216.

(12) Eckerman, C.; Holmbom, B. Method for recovery of compression wood and/or normal wood from oversize chips. Pat. Appl., 2001, PCT/FI01/00691, 22 pp.

(13) Holmbom, B.; Eckerman, C.; Hemming, J.; Reunanen, M.; Sundberg, K.; Willför, S. Method for isolating chemical substances from wood. Pat. Appl., 2002, PCT/FI02/00418, 33 pp.

(14) Eklund, P.; Lindholm, A.; Mikkola, J.-P.; Smeds, A.; Lehtilä, R.; Sjöholm, R. Synthesis of (−)-matairesinol, (−)-enterolactone, and (−)-enterodiol from the natural lignan hydroxymatairesinol. *Org. Lett.* 2003, 5, 491-493.

(15) Ekman, R.; Holmbom, B. Analysis by gas chromatography of the wood extractives in pulp and water samples from mechanical pulping of spruce. *Nord. Pulp Pap. Res. J.* 1989, 4, 16-24.

(16) Örsä F; Holmbom, B. A convenient method for the determination of wood extractives in papermaking process waters and effluents. *J. Pulp Pap. Sci.* 1994, 20, J361-J366.

(17) Ahotupa, M.; Mäntylä, E.; Kangas, L. Antioxidant properties of the triphenylethylene antiestrogen drug toremifene. *Naunyn-Schmiederberg's Arch. Pharmacol.*, 1997, 356, 297-302.

(18) Kawai, S.; Sugishita, K.; Ohashi, H. Identification of *Thuja occidentalis* lignans and its biosynthetic relationship. *Phytochemistry* 1999, 51, 243-247.

(19) Eklund, P. C.; Sillanpää, R.; Sjöholm, R. E. Synthetic transformation of hydroxymatairesinol from Norway spruce (*Picea abies*) to 7-hydroxysecoisolariciresinol, (+)-lariciresinol and (+)-cyclolariciresinol. *J. Chem. Soc., Perkin Trans.* 12002, 16, 1906-1910.

(20) Kolhir, V. K.; Bykov, V. A.; Baginskaja, A. I.; Sokolov, S. Y.; Glazova, N. G.; Leskova, T. E.; Sakovich, G. S.; Tjukavkina, N. A.; Kolesnik, Yu. A.; Rulenko, I. A. Antioxidant activity of a dihydroquercetin isolated from *Larix gmelinii* (Rupr.) Rupr. wood. *Phytother. Res.*, 1996, 10, 478-482.

(21) Saarinen, N.; Joshi, S. C.; Ahotupa, M.; Li, X.; Ämmälä, J.; Mäkela, S.; Santti, R. No evidence for the in vivo activity of aromatase-inhibiting flavonoids. *J. Steroid Biochem. Mol. Biol.*, 2001, 78, 231-239.

(22) Stojanović, S.; Sprinz, H.; Brede, O.; Efficiency and mechanism of the antioxidant action of trans-resveratrol and its analogues in the radical liposome oxidation. *Arch. Biochem. Biophys.*, 2001, 391, 79-89.

(23) Rimando, A. M.; Cuedent, M.; Desmarchelier, C.; Mehta, R. G.; Pezzuto, J. M.; Duke, S. O. Cancer chemopreventive and antioxidant activities of pterostilbene, a naturally occurring analogue of resveratrol. *J. Agric. Food Chem.* 2002, 50, 3453-3457.

The invention claimed is:

1. A method, comprising
adding an antioxidative agent to a substance or composition, wherein said antioxidative agent comprises an extract, obtained by extracting knotwood with a polar solvent and recovering the extract,
wherein knotwood is
i) an over-sized chip fraction, obtained by screening chipped wood which contains knotwood, or
ii) a knotwood-rich subfraction of said over-sized chip fraction, or
iii) knotwood obtained as residue in finishing of mechanical wood products, and
wherein said extract comprises a mixture of at least two components, and
wherein said mixture exhibits a greater antioxidative property than the individual members of the mixture when the antioxidative property is measured as inhibition of lipid peroxidation.

2. The method of claim 1, wherein the knotwood is derived from a wood species selected from the group consisting of *Picea abies, Betula pendula, Pinus sylvestris, Abies sibirica, Pinus sibirica, Abies balsamea, Thuja occidentalis, Pinus cembra, Pseudotsuga menziesii, Larix decidua, Picea glauca, Picea mariana, Picea pungens, Abies pectinata, Abies lasiocarpa, Pinus banksiana, Pinus resinosa, Larix laricina, Larix sibirica, Thuja plicata, Fagus sylvatica, Populus tremula, Tsuga heterophylla* and *Pinus contorta*.

3. The method of claim 1, wherein the substance or composition is a member of the group consisting of elastomers, plastics, petrols, bio-oils, lubricants, adhesives, cosmetics, paper, packaging, paints, dispersions, fungicides, pesticides, herbicides, bacteriocides, insecticides and preservatives.

4. The method of claim 1, wherein said antioxidative agent comprises a fraction of an extract, said extract being obtained by extracting knotwood with a polar solvent and recovering the knotwood extract, followed by withdrawal of at least one component.

5. The method of claim 4, wherein a mixture comprising at least two components is withdrawn from the knotwood extract.

6. The method of claim 5, wherein said antioxidative agent comprises either
i) the withdrawn mixture comprising at least two components, or
ii) a residue of the knotwood extract.

7. The method of claim 6, wherein the withdrawn mixture comprises mainly oligolignans.

8. The method of claim 4, wherein the substance or composition is a member of the group consisting of elastomers, plastics, petrols, bio-oils, lubricants, adhesives, cosmetics, paper and packaging, paints, dispersions, fungicides, pesticides, herbicides, bacteriocides, insecticides and preservatives.

9. The method of claim 1, wherein said extract comprises mainly flavonoids.

10. The method of claim 1, wherein said extract comprises mainly lignans.

\* \* \* \* \*